United States Patent [19]

Miyajima et al.

[11] Patent Number: 4,785,667
[45] Date of Patent: Nov. 22, 1988

[54] METHOD OF MEASURING INCLINING ANGLE OF PLANAR DEFECT OF SOLID MATERIAL BY ULTRASONIC WAVE

[75] Inventors: Takeshi Miyajima, Makabe; Takayuki Oshiro, Niihari, both of Japan

[73] Assignee: Hitachi Construction Machinery Co., Ltd., Tokyo, Japan

[21] Appl. No.: 10,083

[22] PCT Filed: Apr. 22, 1985

[86] PCT No.: PCT/JP85/00225
§ 371 Date: Feb. 11, 1987
§ 102(e) Date: Feb. 11, 1987

[87] PCT Pub. No.: WO86/06486
PCT Pub. Date: Nov. 6, 1986

[51] Int. Cl.[4] ............................................. G01N 29/04
[52] U.S. Cl. ........................................ 73/618; 73/620
[58] Field of Search ................. 73/600, 602, 618, 620, 73/627, 633

[56] References Cited

U.S. PATENT DOCUMENTS

4,299,128  11/1981  Gruber .................................. 73/627
4,524,622   6/1985  Susuki et al. ......................... 73/620
4,531,409   7/1985  Koch et al. ........................... 73/602

Primary Examiner—Tom Noland
Assistant Examiner—Louis M. Arana
Attorney, Agent, or Firm—Wenderoth, Lind & Ponack

[57] ABSTRACT

A method of measuring the inclining angle of a planar defect of a solid material with ultrasonic waves which includes the steps of irradiating ultrasonic waves incident to the planar defect of a solid material while longitudinally scanning a probe forwardly and backwardly. The inclining angle of the planar defect is determined based on the inclination of an echo envelope obtained from the relationship of the echo beam path distances of the ultrasonic waves versus the echo amplitudes or heights of the reflected waves reflected from the planar defect of the solid material. The inclining angle of the defect corresponds to a straight line portion of the echo envelope in a region where the echo height decreased gradually from a maximum height position as the echo beam path distance increases. Measurements can be made non-destructively with one probe and the inclining angle of the planar defect generated within an element or a member forming part of an electronic or mechanical apparatus can be determined accurately in an extremely efficient manner.

7 Claims, 10 Drawing Sheets

$h = -67.9 \log x + 104.3$

○ : Measured value

$h = -40.0 \log x + 66.0$ o : Measured value

Beam passage ($x$)

METHOD OF MEASURING INCLINING ANGLE OF PLANAR DEFECT OF SOLID MATERIAL BY ULTRASONIC WAVE

BACKGROUND OF THE INVENTION

1. Field of the Invention

This invention relates to a method of measuring the inclining angle of a planar defect in various solid materials by utilizing ultrasonic waves.

The planar defect in a solid material in this specification means a flat surface-state defect and hence a planar defect having an area, generated, for example, on a part or component, or a member which constructs an apparatus such as an electric apparatus, a mechanical apparatus or a chemical apparatus in various industrial fields, and involves the state wherein the planar defect is opened on the surface as well as the state wherein the defect is partly opened on the surface, but the state irrespective of the length of the planar defect and the magnitude of the width of the opening. The solid material in this invention involves metal and nonmetal (glass, ceramics, concrete, synthetic resin, rubber and/or wood) and hence a physical body in which ultrasonic waves can be propagated.

Further, the inclining angle of the planar defect in the solid material in this specification means the angle formed between the planar defect in the solid material and the surface or plane of the part or member in which the planar defect is generated.

2. Description of the Prior Art

Figure 16:
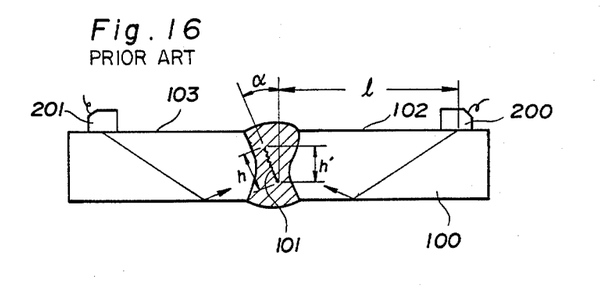
FIG. 16 is a view illustrating the experimental states of two probes for measuring the inclining angle of a crack with respect to the measurement of the amplitude of a welding crack by a conventional defect detecting method.
Figure 17:
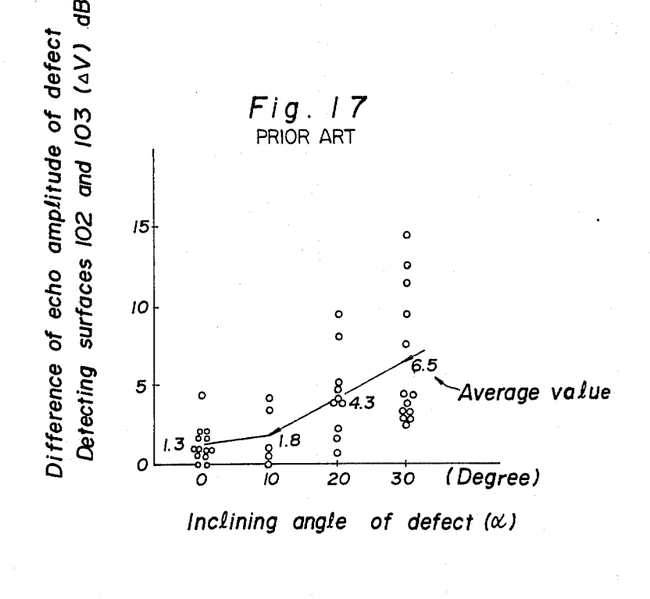
FIG. 17 is a graph showing the experimental results obtained by the experiments shown in FIG. 16.

In the technical field relating to this invention, it is a necessary and important matter to examine the presence or absence of a defect in a part or component, or a member of an apparatus and to know, in the case where the defect exists, the position, shape, type and size of the defect. If there is a planar defect like a crack as type of the defect, in not only the part or member but also destructive dynamics and proposal of countermeasures involving the strength analysis and the lifetime calculation of the entire apparatus, it is important and indispensable to know the type of the planar defect and the inclining angle thereof. There are a number of types of planar defects such as a flat surface defect caused, for example, by improper fusion during the course of welding; a cleavage generated near the surface of a member caused by the fatigue of the member, a thermal stress or a transformation stress upon quenching or tempering or remaining stress during ambient temperature release of the member having the remaining stress; or a crack due to stress corrosion cracking or grain boundary corrosion feasibly generated in a coating material or a heavy metal casing of an atomic reactor fuel used in a corrosive environment or a large-sized storage tank for LPG or gaseous fuel due to tensile stress of a material such as stainless steel or Zr-alloy steel having high tensile strength, toughness and corrosion resistance. The known methods of non-destructively detecting the position and approximate size of a planar defect include detecting the defects by utilizing radiation transmission of X-rays or gamma-rays, of physical energy such as penetration of supersonic waves, magnetic or electric induction, or impregnation with a solution, which are used distinctly according to the types of defects to be detected, i.e., predetermined correlative size. However, there are no known methods of measuring the including angle of the planar defect at present, and the only practical method of measuring a planar defect itself being by taking a photograph of the defect. However, since the result of the test is affected by the results of the taken photograph in this method, it is necessary to provide for selection of film sensitivity and a series of photograph forming steps to the formation of a print, to provide for the shape and the size of an element to be detected in a photographing state, to form a print of high resolution, as well as providing a detecting apparatus having a large scale in consideration the attenuation or scattering of radioactive ray energy due to the material and the size of the element to be detected. In addition, there are special problems with regard to safety during exposure of radioactive rays, thereby resulting in a number of conditions in the measurements. Thus, most cases cannot be simply and accurately measured. The ultrasonic wave flaw detecting method of the other above-described detecting methods offers the possibility of measurements, but most disclosures involve qualitative descriptions relating to the size of the detect instead of the inclining angle of a planar defect, and there is no report of measuring the inclining angle of the planar defect in fact. On the other hand, there is disclosed an experimental report which is based on the assumption that the inclining angle is related to the measurement of the height of a welding crack (in "Non-destructive Inspection", Vol. 26, No. 5, pages 336 to 340, issued in May, 1977). This will be described with reference to FIGS. 16 and 17. FIG. 16 is a view illustrating an experimental state, and this is a method of experimentally measuring with two probes a crack of a planar defect produced by artificially altering a length (h), a height (h') and an inclining angle (alpha) in the butt welded portion of a steel plate with the surfaces of the steel plate at both sides of a welding line as the surfaces to be detected by opposing oblique angle probes in contact with the surfaces, longitudinally scanning the probes forwardly and backwardly. In the figures, numeral 100 denotes a steel plate of an element to be detected (material SS41: JISG 3101 by the Japanese Industrial Standards), one test piece having a thickness of 10.7 mm and sixteen test pieces each having a thickness of 21-24 mm are employed, three cracks 101 are produced within the width of the test piece per one test piece, and experiments are conducted for a total of fifty-one samples. The inclining angle alpha of the crack 101 involves four angles of 0°, 10°, 20° and of the 51 samples 30°, and there are 21 for 0°, 6 for 10°, 9 for 20° and 15 for 30°. The width of one test piece 1 is 150 mm. Numerals 200 and 201 denote probes of model 2.25Z10x18 A 70 (JIS Z 2344). The probes 200 and 201 are opposed in contact on the surfaces 102 and 103 to be detected at both sides of the crack 101, and scanned longitudinally with respect to the crack 101 forwardly and backwardly. The catalytic medium is machine oil. The probes 200 and 201 are connected to a pulse reflection type ultrasonic flaw detecting apparatus (hereinbelow termed as "an ultrasonic flaw detector") of A scope display, (not shown) through a high frequency cable, with the detecting sensitivity of STB-A2-φ4(1S) (JIS Z 2348) as a reference (0 dB). The maximum echoes of the amplitudes $V_A$ and $V_B$ are obtained by the probes 200 and 210 from the crack 101 in the vicinity of skips of 0.75 at the probe distance (the passage of a beam x sin 70°) l of the probes 200 and 201, the absolute value ($\Delta V$) of the difference of both is obtained, and the inclining angle $\alpha$ of the crack 101 is obtained from the correlation of the absolute value $\Delta V$ and the inclining angle $\alpha$ of the crack 101. FIG. 17 is a graph illustrating the experimental results. The ordinate axis of the graph designates the difference ΔV (dB) of the maximum echo amplitudes obtained by the probes 200 and 201, and the abscissa axis designates the inclining angle α (degrees) of the defect. In the graph, a solid line denotes a line for coupling the average values of the measured values in the inclining angle α, and as reported, there is described the degree, "the experimental results have large irregularity, but the inclining angle α of the crack can be presumed approximately from the ΔV", it is accordingly impossible to accurately obtain information from the graph of FIG. 17, and the graph cannot be utilized for a practical purpose.

As described above, since the conventional method of measuring the inclining angle of a planar defect has a number of problems in the measurements, the method cannot readily and accurately measure the defect in a short time nor measure in a real-time. In particular, the measuring method capable of being utilized for a practical purpose by utilizing ultrasonic waves has simple measuring results to be expected, but this method is not yet developed as a practical one at present.

A primary object of this invention is to provide a method of measuring the inclining angle of a planar defect of a solid material by ultrasonic waves which can eliminate the problems and drawbacks of the above-described prior art and accurately and readily measure the inclining angle of a planar defect opened mainly on the surface present on a solid material in an extremely short time without influence of the types, shape, size, inclination of the planar defect and the roughness of the defect surface as well as perform the measurement in a real-time.

Another object of this invention is to provide a method of measuring the inclining angle of a planar defect of a solid material which can measure the defects of a large quantity of elements to be detected by automatically detecting the defect on a manufacturing or inspecting line.

The other objects of the invention will become apparent from the following description.

SUMMARY OF THE INVENTION

This invention is a method of measuring the inclining angle of a planar defect with ultrasonic waves comprising the steps of irradiating ultrasonic waves incident to the planar defect of a solid material while longitudinally scanning a probe forwardly and backwardly and determining the inclining angle of the planar defect from the inclination of an echo envelope obtained from the beam path lengths of the ultrasonic waves and the echo amplitude of the reflected waves reflected from the planar defect in the solid material as an evaluating index by utilizing the inclination of the echo envelope.

The feature of the invention is to utilize the properties to be described in the following, i.e., the properties that the inclination of the echo envelope of the side obtained when the probe is scanned away from the maximum echo amplitude position of the echo envelope has a predetermined correlation to the inclining angle of the planar defect in the solid material. This will be described with reference to FIG. 1 of an explanatory view of the principle of this invention.

Figure 1:
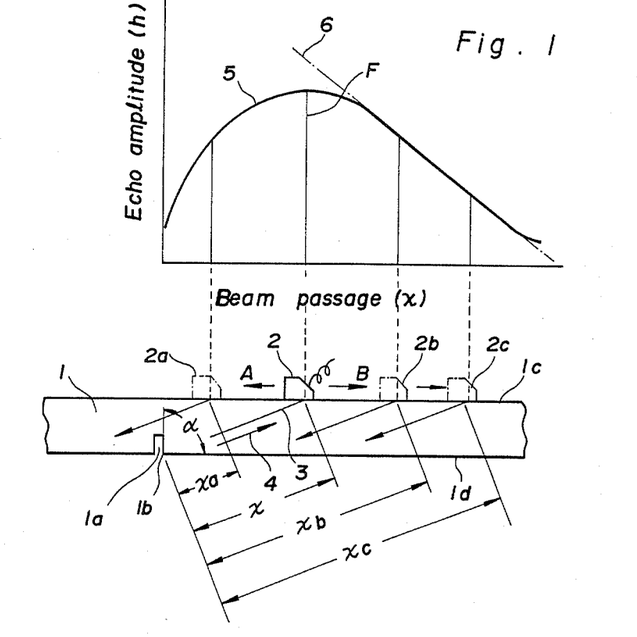
FIG. 1 is an explanatory view of a principle of a method of measuring a planar defect according to this invention.
Figure 2:
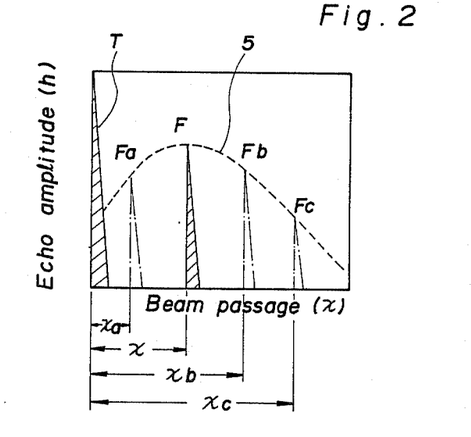
FIG. 2 is an explanatory view showing an echo pattern on a CRT obtained by the method illustrated in FIG. 1.

In FIG. 1, numeral 1 denotes an element to be detected in which the groove 1a of a planar defect opened on the surface is formed to the depth of substantially ½ of the thickness of the element. Symbol 1b denotes the angle of the groove 1a, symbol 1c denotes a defect detecting surface and symbol 1d denotes the surface of the element of the groove 1a side. Symbol α denotes the inclining angle formed between the groove 1a and the surface 1d of the element to be detected. Numeral 2 denotes an inclining angle detecting probe (hereinbelow termed as "an angle beam probe"), which is contacted with the surface 1c to irradiate ultrasonic waves (transversal waves) while longitudinally scanning the angle 1b of the groove 1a in a direction of an arrow A or B forwardly and backwardly. Symbols 2a, 2b and 2c denote the probe located at arbitrary positions when the probe 2 is longitudinally scanned forwardly and backwardly. An incident ultrasonic wave 3 which arrives at the angle 1b is reflected from the angle 1b as a reflecting sound source to become a reflecting wave 4, and is received by the probe 2. When the received reflected wave 4 is displayed on a cathode ray tube (CRT) of A scope display of orthogonal coordinates having the echo amplitude h (dB) in the ordinate axis and the echo beam path distance x (mm) in the abscissa axis at the positions where the probe 2 is longitudinally scanned forwardly and backwardly, there is obtained an echo pattern as shown in FIG. 2. More particularly, a transmitted pulse T is displayed at the position of an origin O on the time base of the CRT, and the echoes of the reflected wave 4 (F, $F_a$, $F_b$, $F_c$ in the drawing) are sequentially displayed at the positions corresponding to the positions longitudinally scanned forwardly and backwardly from the position of the transmitted pulse T, i.e., the positions corresponding to the path distance x (x, $x_a$, $x_b$ and $x_c$ in the drawing) from the incident point to the angles 1b on the surface 1c to be detected by the ultrasonic wave. The echo amplitudes depend upon the distances x of the beams at the positions of the probe 2, and when the vertexes of the respective echo amplitudes (h) of the ordinate axis with respect to the distances (x) of the beams of the abscissa axis at the positions of the probe 2 are coupled by a line, an echo envelope 5 having a vertex at the maximum echo amplitude F is obtained. If the groove 1a is not presented in this case, the reflected wave 4 is not generated, and no echo envelope 5 is obtained. The shape of the echo envelope 5 is determined according to the echo amplitude (h) of sound pressure decided by the product of (the directivity of transmitted wave determined by the vibrator size and the frequency of the probe 2), (the reflecting directivity of the case where the ultrasonic wave is reflected from the groove (planar defect) 1a determined by the position, shape, size, surface roughness and inclining angle of the groove (planar defect) 1a) and (the directivity of the case where the reflected wave 4 is fed through the scattering and the attenuation including the diffraction of the ultrasonic wave). Thus, when the same planar defect is detected with the same probe, the directivity of the vibrator and hence transmitted and received waves is constant, the shape of the echo envelope thus obtained is also constant, and the shape of the envelope is determined only by the reflecting directivity varying with respect to the position and the inclining angle of the planar defect. In the case as shown in the drawings, the position, shape and size of the groove (planar defect) 1a are as described above, and the surface roughness is approx. 20 micron of average roughness, and the inclining angle α for the echo envelope 5 shown is 90°. When the inclining angle α of the groove 1a as shown is gradually varied from 90° at small angles toward an acute angle side and the probe 2 is longitudinally scanned forwardly and backwardly, the shape of the echo envelope 5 thus obtained gradually becomes more narrow in the reflecting directivity at the maximum echo amplitude F as a center, the inclination of the echo envelope 5 obtained when scanned to the side that the distance x of the beam is increased in length from the position of the maximum echo amplitude F, i.e., the side that scanned to the direction of an arrow B becomes abrupt, and the envelope has the inclination of a substantially rectilinear line as shown by the one-dotted chain line 6 in FIG. 1. The method of determining the inclining angle of the planar defect of this invention is to measure the inclining angle of the planar defect by utilizing a predetermined correlation which exists between the inclining angle of the planar defect and the inclination of the linear line of the echo envelope of the side on which the distance of the beam becomes longer from the maximum echo amplitude position of the echo envelopes. Since the echo envelope can be readily obtained from the echo amplitude of the reflected wave displayed on the CRT in response to the various properties of the planar defect including the inclining angle, the correlation to the inclining angle of the planar defect can be simultaneously obtained readily. Therefore, in comparison with the conventional method of obtaining the inclining angle from the difference of the maximum echo amplitudes with two probes from both sides of the planar defect, the method of this invention can accurately measure the inclining angle of the planar defect opened on the surface of a member mainly of an element to be detected by longitudinally scanning one probe forwardly and backwardly in an extremely short time in a real-time without limit in the properties of the planar defect. This feature of the invention can readily measure a large quantity of elements to be detected by automatically detecting the planar defects.

The foregoing description has been with respect to the planar defect opened on the surface of the element to be detected. The properties of the feature of the invention can be also utilized for planar defect not opened on the surface of the element to be detected, though partly under certain conditions. More specifically, the condition is that the nearest distance from the surface of a member to the planar defect is approx. ½ or less of the wavelength of the frequency of the used probe. Since the planar defect under this condition has a small gap of approx. 1 mm between the planar defect and the surface of the member as a reflecting sound source similar to the angle 1b in FIG. 1, the incident ultrasonic wave is reflected similarly to the angle 1b from the sound source. Therefore, the echo envelope can be obtained by the same method as in the case of the opened defect, and the inclining angle of the planar defect not opened on the surface can be measured similarly to the case of the opened defect.

The correlation between the inclination of the above-described echo envelope and the inclining angle of the planar defect will be described in more detail as follows.

BRIEF DESCRIPTION OF THE DRAWINGS

FIGS. 3 to 12 are explanatory views a first embodiment of this invention, wherein

FIGS. 13 to 15 are explanatory views of a second embodiment according to this invention, wherein

DETAILED DESCRIPTION OF THE PREFERRED EMBODIMENTS

A first embodiment of the present invention will be described in detail with reference to FIGS. 3 to 12. In the drawings, the same reference numerals and symbols as those in FIGS. 1 and 2 denote the same or equivalent elements and members.

Figure 3:
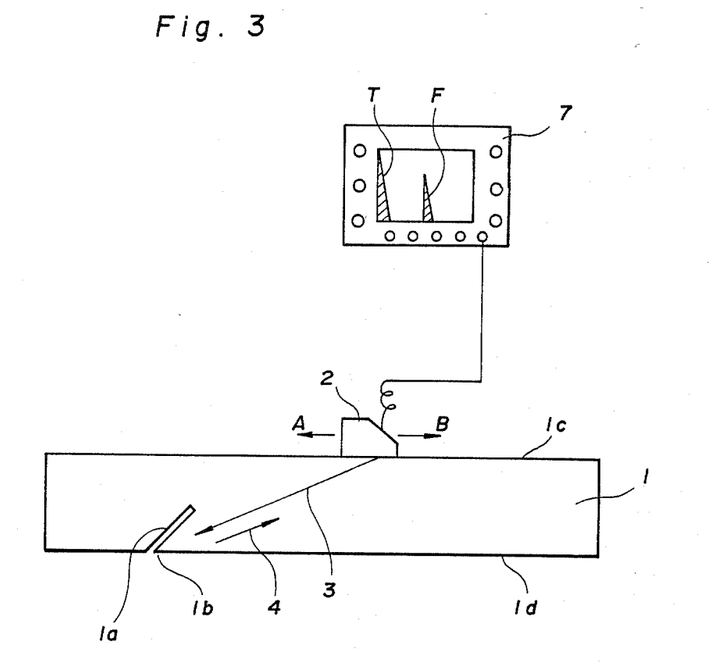
FIG. 3 is an explanatory view of the general characteristics thereof.
Figure 4:
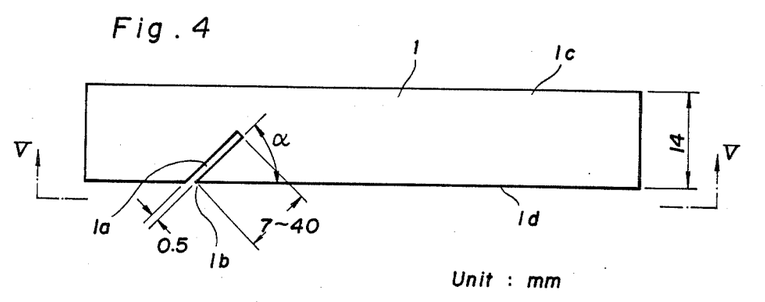
FIG. 4 is a side view of an element to be detected and used in the embodiment of FIG. 3.
Figure 5:
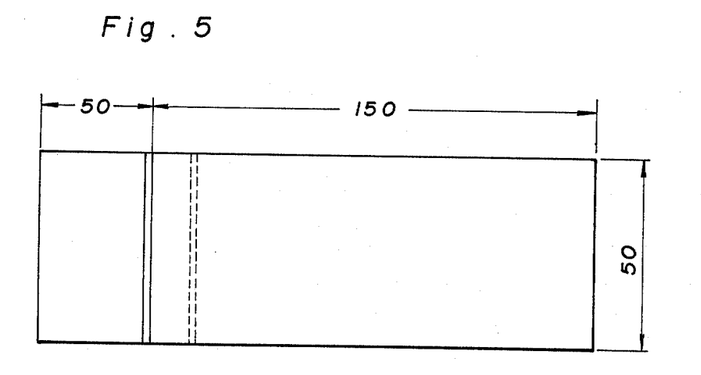
FIG. 5 is a view as seen from arrows V—V of FIG. 4.

In FIG. 3, a probe 2 is connected to an ultrasonic defect detector 7 through a high frequency cable. When the probe 2 is longitudinally scanned forwardly and backwardly on a defect detecting surface 1c in a direction of an arrow A or B with respect to the edge 1b of a groove 1a, an incident ultrasonic wave 3 is reflected at the edge 1b as a reflecting sound source, and displayed together with a transmitted pulse T at positions corresponding to the distance of the beam of the incident ultrasonic wave 3 on a CRT as the echo F of the reflected wave 4. The probe 2 used irradiates 2.25 MHz of frequency at 2.25Z10×18A70 (JIS Z-2344) of refractive index of 70° with a vibrator of 10 mm×18 mm in size. The shape and the side of elements 1 to be detected and used in the method of this embodiment are shown in FIGS. 4 and 5. A steel plate (having SS41 JIS G 3101) 14 mm (thick), 200 mm (length)×50 mm (width) is used, and a planar defect 1a having a depth 7 mm to 40 mm and a width x of ½ of 0.5 mm is formed at a position slightly near a surface 1d opposite to the defect detecting surface 1c. The inclining angles α of the planar defect 1a fall within eight types which include 10°, 15°, 22.5°, 30°, 45°, 60°, 80° and 90°. The machining accuracy of the portions is approx. 20 microns (μm) (JIS B 0601) of average roughness of the defect detecting surface 1c, the surface 1d and the planar defect 1a, and the others are similarly approx. 35 micron to 100 micron. The results measured by the method shown in FIG. 3 for inclining angles α of 10°, 45° and 90° (which comprise three of eight types of the inclining α) are shown in FIGS. 6 to 11.

Figure 6:
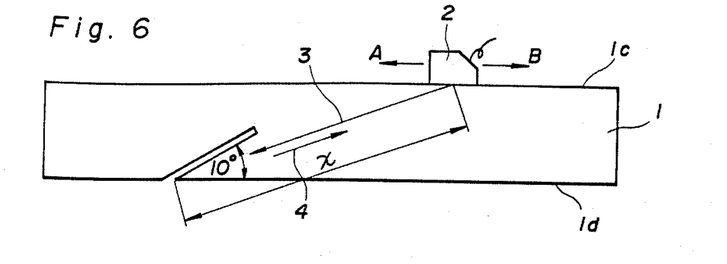
FIG. 6 is an explanatory view of scanning an element to be detected having a 10° inclining angle of a planar defect in the element to be detected in FIG. 4.
Figure 7:
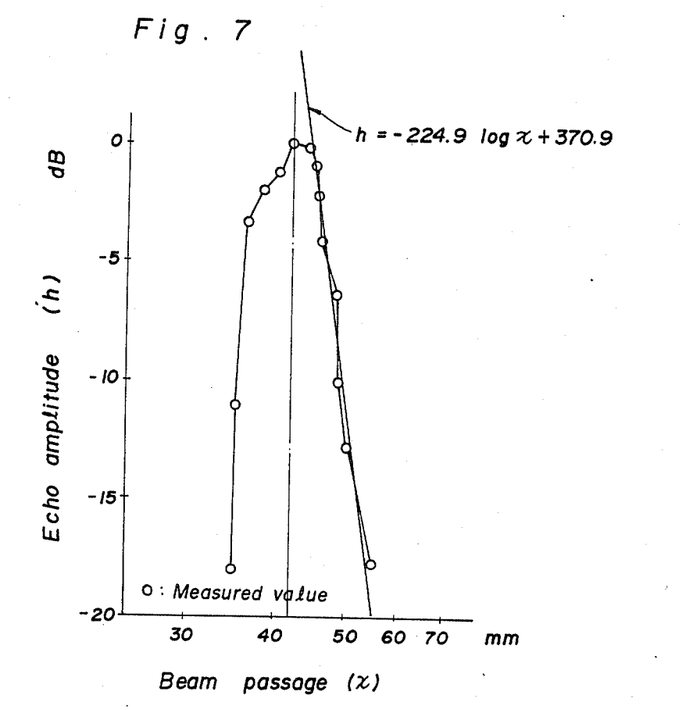
FIG. 7 is a graph illustrating an envelope obtained from the relationship between the distance of the beam and the echo amplitude by the method shown in FIG. 6.
Figure 8:
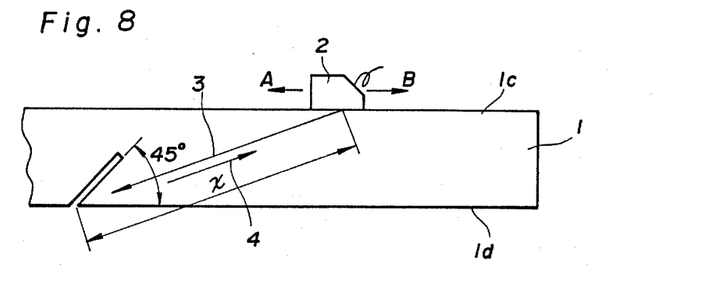
FIG. 8 is an explanatory view of scanning an element to be detected having a 45° inclining angle of a planar defect.
Figure 9:
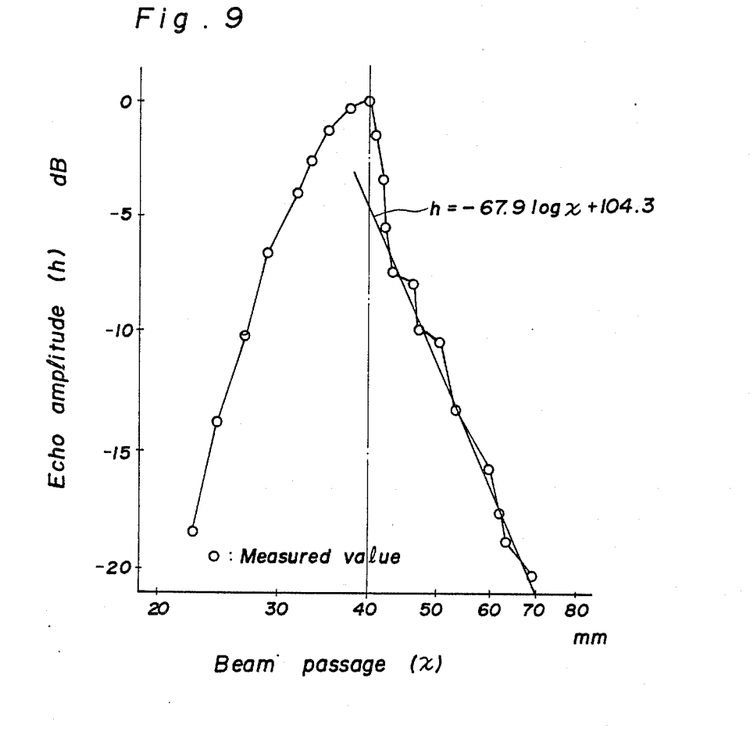
FIG. 9 is a graph illustrating an envelope obtained by a method shown in FIG. 8.
Figure 10:
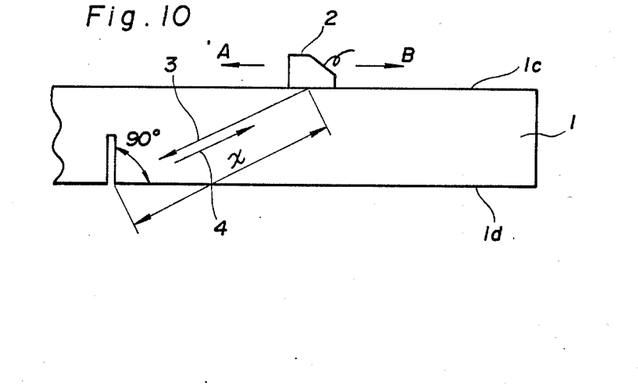
FIG. 10 is an explanatory view of scanning an element to be detected having a 90° inclining angle of a planar defect.
Figure 11:
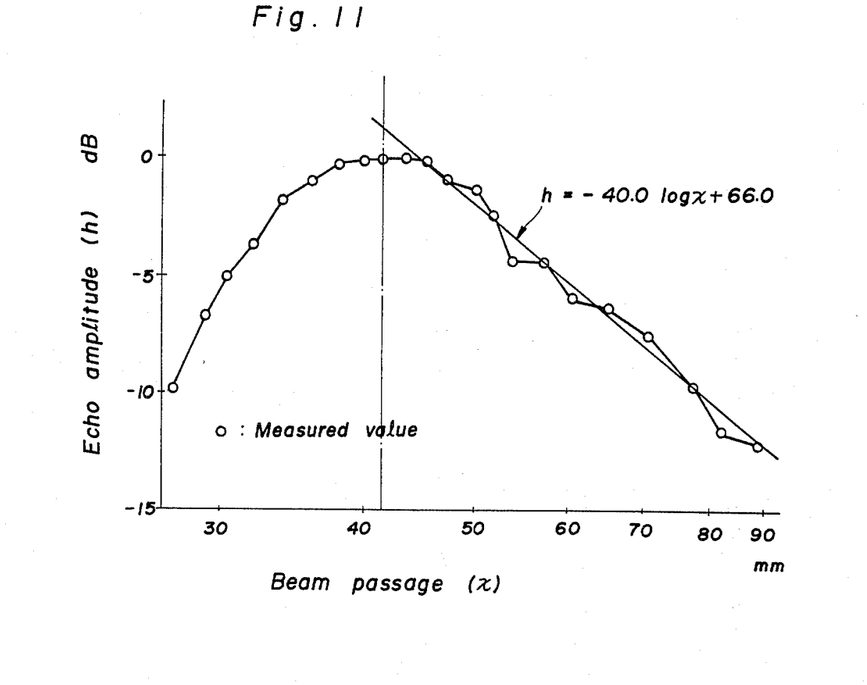
FIG. 11 is a graph illustrating the envelope obtained by a method shown in FIG. 10.

FIG. 6 shows a view of the measuring procedure in the case where the inclining angle α is 10°. When the echo amplitude h of the reflected wave 4 of the various distances x of the beam of the incident supersonic wave 3 is plotted, a graph in FIG. 7 illustrating the echo envelope is obtained. Similarly, FIG. 8 is a view of the measuring procedure in the case where the inclining angle is 45°, and FIG. 9 is a graph illustrating the echo envelope obtained by the measurement. FIG. 10 is a view of the measuring procedure in the case where the inclining angle α is 90°, and FIG. 11 is a graph illustrating the echo envelope obtained by the measurement. In the graphs showing the echo envelopes of FIGS. 7, 9 and 11, the abscissa axes indicate logarithmic values of the distance x (unit: mm) of the beam, and the ordinate axes indicate the maximum value of the echo amplitude h of reference sensitivity (0 dB), wherein "o" illustrates the measured value. Then, when returning formulae are separately obtained at each inclining angle α by the minimum squaring method in a measuring range wherein the probe 2 is scanned in a direction of an arrow B away from the planar defect from the maximum echo amplitude (0 dB) of a graph showing the echo envelopes, the formulae are as listed in the following table.

| Inclining angle α | Returning formulae |
| --- | --- |
| 10° | h = −224.9 log x + 370.9 |
| 45° | h = −67.9 log x + 104.3 |
| 90° | h = −40.0 log x + 66.0 |

The returning formulae in the above table become linear lines shown by solid lines in the drawings, and the echo beam height or amplitude h can be arranged in a simple formula as below irrespective of the inclining angle α.

$$h = -a \log x + b \quad (1)$$

where
a = proportional constant (indicating the inclination of the returning formula)
b = constant (the value of the returning formula in the above table is the value of the echo amplitude h in the case where the distance of beam x=1)
x = the echo beam path distanct (Unit: mm)

Figure 12:
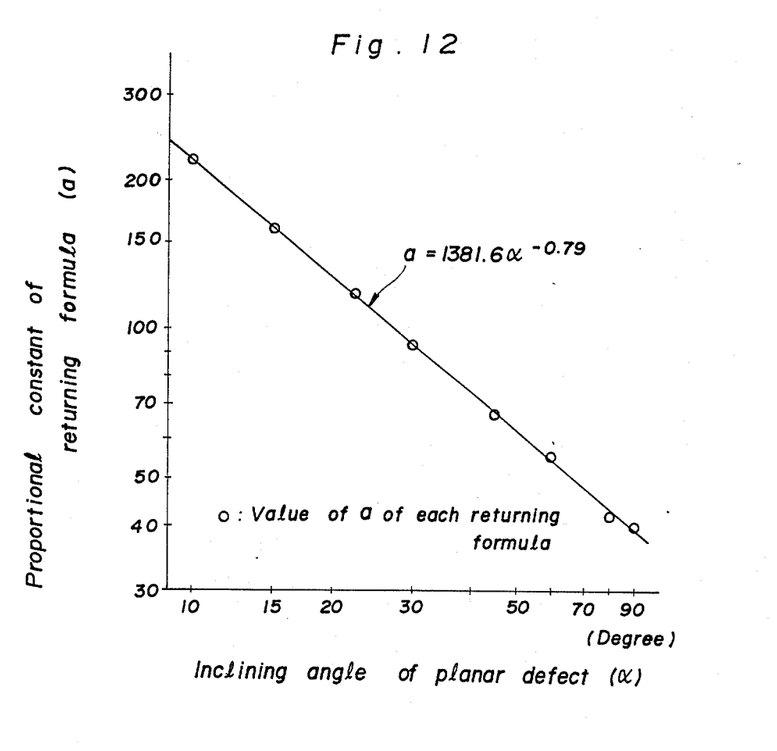
FIG. 12 is a graph illustrating the correlation between the inclining angle (a) of a planar defect formed in an element to be detected as shown in FIG. 4 and the proportional constant showing the inclination of the envelope of a returning formula obtained by the method in FIG. 3.
Figures 13A, 13B, 13C:
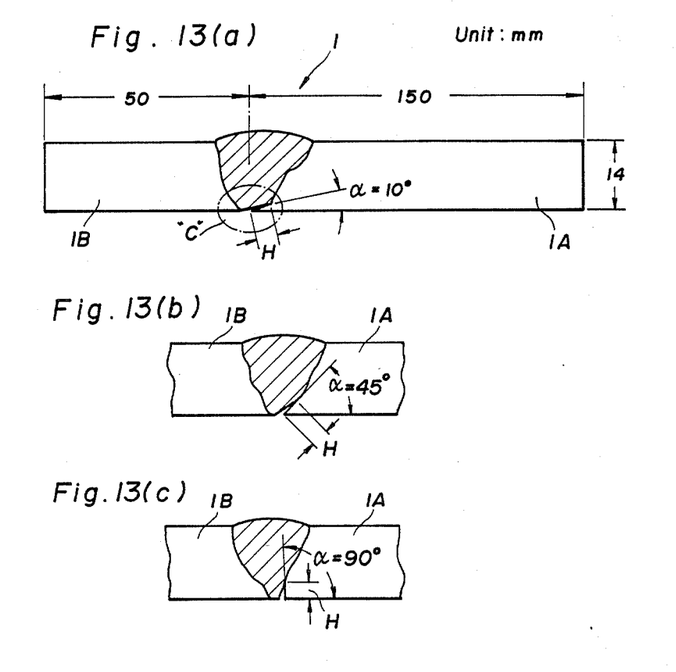
FIG. 13(a) is a side view of an element to be detected in the case where the inclining angle of a planar defect used for the embodiment is 10°.
FIG. 13(b) is a view of the case where the inclining angle is 45°.
FIG. 13(c) is a view of the case where the inclining angle is 90°.

When the returning formulae in the above table are compared, the smaller the values of the proportional constants "a" showing the inclination of the returning formula are, the larger the inclining angle α becomes. This demonstrates that the inclination of the returning formula is large. This is clearly shown in the drawings. When the remaining elements to be detected (the remaining five types of inclining angles) are measured similarly to the above three types to obtain the returning formulae and the relationship between the proportional constants "a" of the respective returning formulae and the inclining angles α of the planar defects is summarized, FIG. 12 is obtained. In the drawing, the abscissa axis indicates the logarithmic value of the inclining angle α (Unit: degree), and the ordinate axis indicates the logarithmic value of the proportional constant "a". In the drawing, the mark "o" denotes the values of the proportional constant "a" of the returning formulae plotted. When the marks "o" are coupled, one linear line is obtained showing that both have excellent linear correlation. The more the inclining angle of the planar defect increases, the less the value of the proportional constant "a" decreases. When the returning formulae of the graph is obtained by the minimum squaring method, the following formula is obtained.

$$a = 1381.6 \alpha^{-0.79} \quad (2)$$

The above formula (2) can be modified to the following formula:

$$\alpha = 10^{(\frac{3.14 - \log a}{0.79})} \quad (3)$$

As understood from the formula (3), the inclining angle of the planar defect can be readily obtained if the value of the proportional constant "a" of the returning formula is obtained. When the echo envelope obtained from the echo amplitude of the reflected wave of the various passages of the beam of the incident ultrasonic wave is obtained as described above, the value of the proportional constant "a" of the returning formula can be obtained from the inclination of the echo envelope of the side in the direction for separating the probe from the maximum echo amplitude position of the echo envelope from the planar defect, i.e., obtained by scanning the probe away from the planar defect.

As understood from the description of this embodiment, the method of measuring according to the invention is conducted by reflecting the incident ultrasonic wave irradiated from the probe at the angle of the groove of the planar defect mainly as a reflecting sound source and displaying the echo on the CRT. Since the angle of the groove represents the angle of the planar defect, the method of the invention can be applied not only as to a planar defect as in this embodiment, but also to the measurement of the angle of the element or member which does not need the severe preciseness like the measurement of the groove angle of welding.

The above-described first embodiment has been described in the case where a planar defect of high machining accuracy was artificially formed in the element to be detected. Now, a second embodiment of the measuring method of the invention applied to a planar defect generated due to a welding improper fusion of the groove will be described in detail with reference to FIGS. 13(a) to 13(c) to 15.

Figure 14:
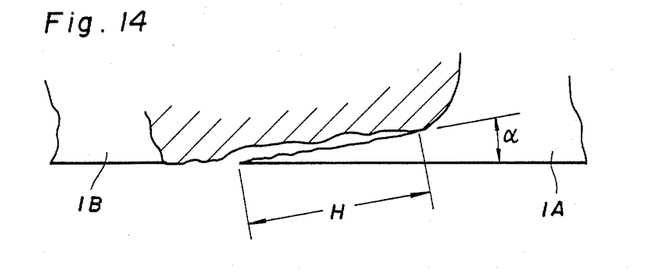
FIG. 14 is a detailed view of the portion "C" of FIG. 13(a)

Elements to be detected and used in this second embodiment are shown in FIGS. 13(a) to 13(c) and 14. A total of 24 elements 1 are prepared, and a member 1A having dimensions of 14 mm (thickness)×150 mm (length)×50 mm (width) and a member 1B having the same thickness and width as the member 1A but a length of 50 mm are to be connected through a groove 5 in such a manner that the inclining angle of a planar defect becomes the same as the first embodiment by butt welding. The material is the same as the SS41 and the probe used is the same as the 2.225Z10×18A70 of the first embodiment. The planar defect generated due to the improper fusion of the groove is measured according to the method of this invention, then cut and actually measured. The results exhibit all the planar defects opened on the surface with the length H of the defect (the defect amplitude when the inclining angle α is 90°) being 1.3 to 7 mm. The inclining angles α are 3 out of eight possible types of 10°, 15°, 22.5°, 30°, 45°, 60°, 80° and 90°, and substantially the same types as those of the first embodiment are obtained. The states of the planar defects of the cases are shown for the inclining angle $\alpha = 10°$ in FIG. 13(a), for the inclining angle $\alpha = 45°$ in FIG. 13(b) and for the inclining angle $\alpha = 90°$ in FIG. 13(c). FIG. 14 shows the detail of the portion "C" in FIG. 13(a), and the defect surfaces exhibit roughness on the groove or fusion-bonded metal surface of the elements to be detected as shown, and the width of the defect is 0.1 to 0.2 mm. The above-mentioned elements are measured by the same method as in the first embodiment and the results are summarized in FIG. 15. In the graph, the abscissa axis indicates the values of the intrinsic inclining angles $\alpha_R$ (Unit: degree) actually measured by cutting the elements, and the ordinate axis indicates the inclining angle $\alpha_U$ (Unit: degree) measured by the method of this invention. The measured values are denoted by solid mark "✳". In the drawings, when the measured value of the element of approx. 10° of the inclining angle α is, for example, observed, the inclining angles $\alpha_R$ of the actually measured value of the three elements by cutting the element are all approx. 10°, but the inclining angle measured according to the method of the invention are approx. 8°, 9° and 12°. In the element of approx. 45° of the inclining angle $\alpha_R$, the inclining angles $\alpha_U$ are 41°, 44°, 48.5° and in the element of approx. 90°, the inclining angles $\alpha_R$ are 86°, 87.5° and 91°. When the average value ($\bar{x}$) and the standard deviation ($\sigma$) of the measuring error ($\alpha_U - \alpha_R$) are obtained for all the measured values, the following values are obtained.

$\bar{x} = +0.08°$ $\sigma = 2.37°$

Figure 15:
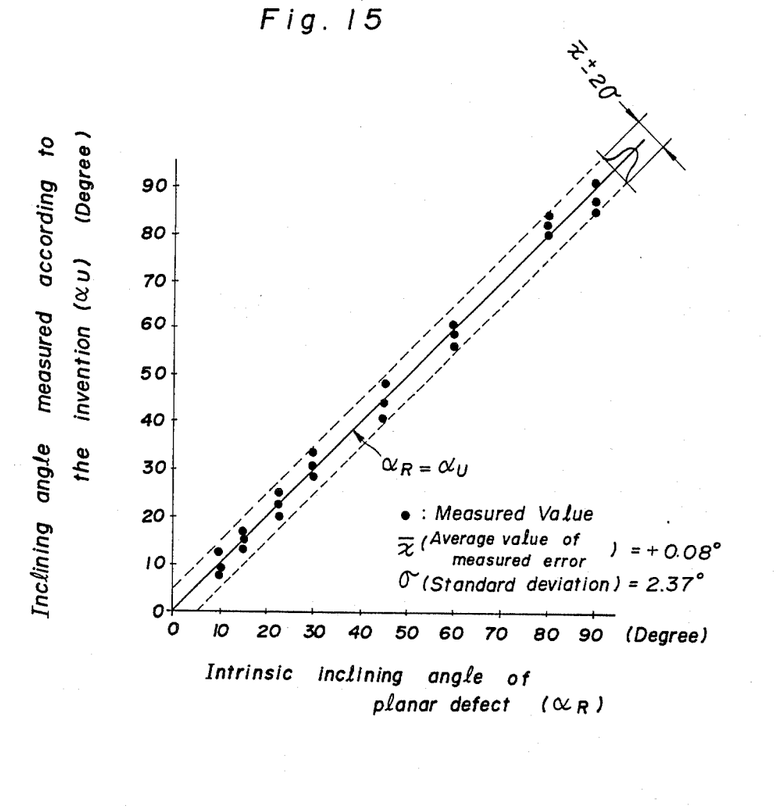
FIG. 15 is a graph for explaining the measuring error of the inclining angle measured according to this invention.

The measured values are all concentrated to extremely near the linear line in the drawing of 45° of an ideal value ($\alpha_R = \alpha_U$), contained with large margins within the range of ($\bar{x} \pm 2\sigma = 4.82°$) as designated by a broken line in parallel with the linear line to thereby prove the excellent accuracy of the measurement according to the method of the invention. In the embodiments described above, the length H of the defect is distributed to a range of 1.3 mm to 7 mm as described above, and accurately measured values can be obtained without influence of the length of the length H of the detect. This is presumed from the reason that, if the inclining angles α of the planar defects are equal, the echo amplitude h on the CRT increases or decreases according to the length of the length H of the defect so that the dB values of the obtained envelopes are different but the inclinations of the envelopes of the side for scanning from behind the postion of the maximum echo amplitude are all equal. The fact that the measured inclining angle of the planar defect is not affected by the influence of the length H of the defect exhibits the possibility that the small angle of a small defect which cannot be measured by an ordinary angle measuring instrument can be measured. On the other hand, the defect surface is ordinarily rough similarly to this embodiment such as sawtooth shape of irregular heights, folded or bent surface, or composite surface of them. The fact that the accurately measured values are obtained in the embodiments described above also demonstrates that the defect surface having the complicated inclination of the sawtooth state, folded and bent surfaces can be measured to produce the envelope on the CRT with the average inclination of them, and when the inclination of the envelope is calculated, the measured inclining angle of the defect surface can be obtained without influence of the surface roughness. This can be generally applied to the measurements of the opened crack or opened defect in the bead stopping end of welding due to the above-described stress corrosion crack or Hertz stress generated over the depth of 0.1 mm to several mm from the surface.

The proportional constant "a" and the constant "b" of the formula (1) are determined by the acoustic characteristic of the material of the element to be detected, and when the solid materials of various materials are obtained by experiments, the inclining angles of the planar defects can be accurately measured extremely simply and readily in the same manner as the first and second embodiments described above.

The method described above relates to a method of measuring visually by displaying the echo or the reflected wave on the CRT. However, it is also possible to represent the values of analog values of the echo amplitude and the distance of the beam together with inclining angles without displaying them on the CRT by digitizing the analog values of the echo amplitude and the passage of the beam by the means ordinarily used by those skilled in the art in this field and further calculating the analog amount in a relation formula correlative to the inclining angle of the planar defect to numerically express the values together with the inclining angle. Further, it is also possible to diagnose a defect in a piece of equipment and preventively diagnose it or to automatically measure a large quantity of elements to be detected in a manufacturing line by storing the numeric values in a memory and comparing them with a reference value or threshold value.

This invention is not limited to the particular embodiments described above. Various other changes and modifications may be made within the spirit and scope of the present invention.

What is claimed is:

1. A method of measuring an angle of a planar defect within a plate-like solid material with ultrasonic waves wherein said defect opens or substantially opens at a location of a first surface of said solid material with an angle of up to 90 degrees with respect to said first surface, and wherein an angle beam probe is applied on a second surface opposite to the first surface of the solid material, and ultrasonic wave beam pulses are transmitted into the solid material while said angle beam probe is traversed along said second surface in a direction towards and away from the planar defect, said traversing being carried out at least within a region where said beam is incident to and irradiates said location at which said defect opens or substantially opens comprising the steps of:

receiving with said probe each reflected wave which is reflected mainly from said location of the planar defect corresponding to each beam path;

detecting each echo height of each reflected wave;

obtaining a polygonal line forming an echo envelope in an orthogonal coordinate system defined by the echo heights and the logarithmic values of the each beam path distances and obtaining an inclination of a portion of the echo envelope corresponding to a substantially straight line in a region wherein the echo height decreases gradually from a maximum height position as the echo beam path distance increases; and     determining the angle of the planar defect by comparing the obtained inclination of the straight line portion of the echo envelope and predetermined reference inclinations of the planar defect.

2. A method of measuring an angle of a planar defect within a plate-like solid material to be tested with ultrasonic waves wherein said defect opens at a location of a first surface of said solid material with an angle of up to 90 degrees with respect to said first surface and wherein an angle beam probe is applied on a second surface opposite to the first surface of the solid material and ultrasonic wave beam pulses are transmitted into the solid material while said angle beam probe is traversed along said second surface in a direction towards and away from the planar defect, said traversing being carried out at least within a region where said beam is incident to and irradiates said location at which said defect opens comprising the steps of:

preparing a plurality of plate-like samples of said solid material having artificially introduced defects with different angles with respect to said first surface;

moving the angle beam probe over the second surface of each of the samples and receiving with said probe each reflected wave which is reflected mainly from said location of each of the artificially introduced planar defects corresponding to each beam path;

detecting each echo height of each reflected wave;

obtaining a polygonal line forming an echo envelope in an orthogonal coordinate system defined by the echo heights and the logarithmic values of the echo beam path distances and obtaining an inclination of a portion of the echo envelope corresponding to a substantially straight line in a region wherein the echo height decreases gradually from a maximum height position as the echo beam path distance increases for each of the samples;

determining returning formulas for the respective angles of the artificially introduced planar defects based on the obtained inclination of the straight line portion of each of the echo envelopes to obtain predetermined reference inclinations of the artificially introduced planar defects;

moving said angle beam probe along said second surface of said material to be tested in a direction towards and away from the planar defect therein said traversing being carried out at least within a region where said beam is incident to and irradiates said location at which said defect opens;

receiving with said probe each reflected wave which is reflected mainly from said location of the planar defect in the material to be tested corresponding to each beam path;

detecting each echo height of each reflected wave in the material to be tested;

obtaining a polygonal line forming an echo envelope in an orthogonal coordinate system defined by the echo heights detected for the material to be tested and the logarithmic values of the echo beam path distances and obtaining an inclination of a portion of the echo envelope corresponding to a substantially straight line in a region wherein the echo height decreases gradually from a maximum height position as the echo beam path distance increases; and     determining the angle of the planar defect by comparing the obtained inclination of the straight line portion of the echo envelope for the material to be tested with said predetermined reference inclinations of the artificially introduced planar defects.

3. A method of measuring an angle of a planar defect within a plate-like solid material by means of ultrasonic waves wherein said defect is located adjacent a first surface of said material and forms an angle of up to 90 degrees therewith, comprising:

predetermined reference inclinations of portions of reference echo envelopes, each of which corresponds to a substantially straight line in a region wherein echo heights decrease gradually from a maximum height position as an echo beam path distance increases, said echo envelopes being respectively obtained by moving an angle beam probe along second surfaces of samples of said material having artificially introduced planar defects therein at different angles with respect to first surfaces of the samples opposite to said second surfaces, said angle beam probe transmitting ultrasonic wave beam pulses into said samples such that said beam is incident to said planar defects and receiving reflected waves reflected from said planar defects, said echo envelopes being generated by a plot of echo heights of said reflected waves versus echo beam path distances corresponding to different positions of said angle beam probe along said second surfaces;

measuring an angle of a planar defect within a plate-like solid material other than said samples by means of said ultrasonic waves wherein said defect is located adjacent a first surface of said material and forms an angle of up to 90 degrees therewith by comparing an inclination of a portion of a non-reference echo envelope to said predetermind reference inclinations of portions of said reference echo envelopes, said inclination of said portion of said non-reference echo envelope corresponding to a substantially straight line in a region wherein echo heights decrease gradually from a maximum height position as an echo beam path distance increases, said non-reference echo envelope being obtained by moving an angle beam probe along a second surface of said material having said defect therein at an angle with respect to a first surface opposite to said second surface, said angle beam probe transmitting ultrasonic wave beam pulses into said material such that said beam is incident to said defect and receiving reflected waves reflected from defect, said echo envelope being generated by a plot of echo heights of said reflected waves versus echo beam path distances corresponding to different positions of said angle beam probe along said second surface.

4. The method of claim 3, wherein said angle beam probe is moved toward and away from said defect during said moving step.

5. The method of claim 3, wherein said plot of echo heights of reflected waves versus echo beam path distances comprises logarithmic values on both axes of said plot.

6. The method of claim 3, further comprising a step of developing returning formulae, each of which corresponds to one of said angles of said artificially introduced defects, said returning formulae being represented by the formula: $h = -a \log x + b$, wherein "a" is a proportional constant indicating an angle of respective one of said returning formulae corresponds to, b is a constant, x is the echo beam path distance, and h is the height of the echo beam.

7. The method of claim 6, where lower valves of "a" correspond to higher values of of the angle of the defect.

* * * * *